United States Patent [19]
Kreutner

[11] Patent Number: 5,291,883
[45] Date of Patent: Mar. 8, 1994

[54] TRANSCUTANEOUS ELECTRIC NERVE STIMULATION SYSTEM

[75] Inventor: Bernd Kreutner, Ehringhausen, Fed. Rep. of Germany

[73] Assignee: Pierenkemper GmbH, Ehringhausen, Fed. Rep. of Germany

[21] Appl. No.: 627,092

[22] Filed: Dec. 13, 1990

[30] Foreign Application Priority Data

Mar. 9, 1990 [DE] Fed. Rep. of Germany ....... 4007542

[51] Int. Cl.$^5$ ............................................. A61N 1/40
[52] U.S. Cl. ................................................ 128/421
[58] Field of Search ......................... 128/421, 422, 423

[56] References Cited

U.S. PATENT DOCUMENTS

| 3,563,247 | 2/1971 | Bowers | 128/422 |
| 4,558,703 | 12/1985 | Mark | 128/421 |
| 4,674,482 | 6/1987 | Waltonen et al. | 128/423 R |

FOREIGN PATENT DOCUMENTS

| 0026479 | 4/1981 | European Pat. Off. |
| 2843922 | 4/1979 | Fed. Rep. of Germany . |
| 3431027 | 7/1985 | Fed. Rep. of Germany . |
| 8910361 | 1/1990 | Fed. Rep. of Germany . |
| 1070409 | 5/1955 | France . |

OTHER PUBLICATIONS

Kunitoshi Aono, Patent Abstracts of Japan, Vol. II, Nr. 374 (E-562) [2821], December 5, 1987; and JP-A-62 141 814, June 25, 1987.

Donaldson et al., "When are actively balanced biphasic ('Lilly') stimulating pulses necessary in a neurological prosthesis?", Medical & Biological Engineering & Computing, Jan. 1986, pp. 41–49.

Primary Examiner—William E. Kamm
Assistant Examiner—Scott M. Getzow
Attorney, Agent, or Firm—Robert J. Koch

[57] ABSTRACT

An apparatus for transcutaneous electric nerve stimulation (TNS) with a power supply, a frequency generator and an electric circuit for the generation of different output frequencies of variable intensity at the output electrodes which may be connected to the apparatus and to an output short circuit to improve the pulse form emitted. The output short circuit network comprises a transistor T1, which upon actuation by a triggering pulse activates with its collector the base of a subsequent transistor T2, in a manner such that the trigger pulse is inverted in the transistor T1, whereby the transistor T2 switches to the negative pulse flank and the outlet is short-circuited by the discharge resistor R(ent) connected to the emitter side.

15 Claims, 2 Drawing Sheets

TRANSCUTANEOUS ELECTRIC NERVE STIMULATION SYSTEM

BACKGROUND OF THE INVENTION

1. Field of the Invention

The invention relates to an apparatus for transcutaneous electric nerve stimulation (TNS) with a power supply, a frequency generator and an electric circuit for variable frequency and intensity electrode output signals connectable with the apparatus and an output short circuit to improve the pulse form emitted.

2. Description of the Related Technology

Various kinds of painful conditions have been treated by electric nerve stimulation by stationary devices. These methods are standard physical therapy. These processes involve application of current to the skin. A high stress is applied to the skin by a direct current and currents of a DC character. However, the depth of current penetration, which is important to the treatment of numerous painful conditions, is very low.

Only by the development of electronic structural elements, in particular semiconductors, has it been possible to produce pulsed currents and frequencies of different kinds and to determine their therapeutic effects.

By virtue of technical developments in the field of power sources and electronic miniaturization, small portable therapy devices suitable for adequate continuous use were developed. The decisive difference between the high voltage devices designed for stationary use and the portable TNS is merely different power outputs. An effective and adequate current density may be obtained with TNS devices by the use of relatively small electrode surfaces, which are entirely sufficient, as the concentration and strength of this form of treatment applies to local pain therapy.

It was found in actual practice that the pulse form emitted by TNS devices is not entirely suitable for the actual characteristics of TNS applications. Current intensity measurements were performed heretofore on a purely ohmic load resistor, with their value amounting in most cases in about 1 KOhm. The resultant pulse form corresponds to a square pulse with steep flanks.

It has been discovered in practice that the equivalent network diagram does not consist of purely ohmic resistors, but of a series of horizontal load resistors with a parallel connected capacitor on one resistor. The pulse forms obtained in this manner greatly differ from those mentioned above.

It has been found that the dimensioning of the structural elements in the simplified equivalent network diagram depends on a number of parameters, i.e., the type of skin of the patient, the electrode gel used, the electrodes and the frequency applied.

It was also discovered that the current measured on the patient is higher than at the 1 KOhm measuring resistor. Finally, the voltage pulse determined on the patient is strongly rounded, i.e., the rise flattens after a steep onset to a maximum, which decreases steeply and declines asymptotically. The correct pulse is saw-tooth like, with a strongly negative pulse.

SUMMARY OF THE INVENTION

It is an object of the invention to provide a circuit generating pulse forms corresponding to the pulse forms measured on the patients.

This object is attained by exposing a transistor T1 to the actuating pulse. The collector of T1 is connected to the base of a subsequent transistor T2. Transistor T1 activates in a manner such that the triggering pulse is inverted in transistor T1 and connects following the negative pulse flank. The outlet is short circuited over the discharge resistor R(ent) connected on the emitter side.

According to the invention, the base of the transistor T1 of the output short circuit is connected by an inlet resistor R1 to the triggering. The collector of the transistor T2 is further connected to one outlet pole and the discharge resistor R(ent) connected to the transistor T2 with the other outlet pole.

Advantageously, according to the invention, the pulse repeat frequency amounts to a maximum of 160 Hz.

The current pulse form is saw tooth like, with a steep negative descending flank, while the voltage pulse form has an ascent with a steep onset, flattens to a maximum, which then declines steeply.

The equivalent network diagram is a horizontal load resistor in series with a capacitor connected in parallel to one resistor.

The invention will become more apparent from the following description with reference to the drawings.

DETAILED DESCRIPTION OF THE PREFERRED EMBODIMENT

Figure 1:
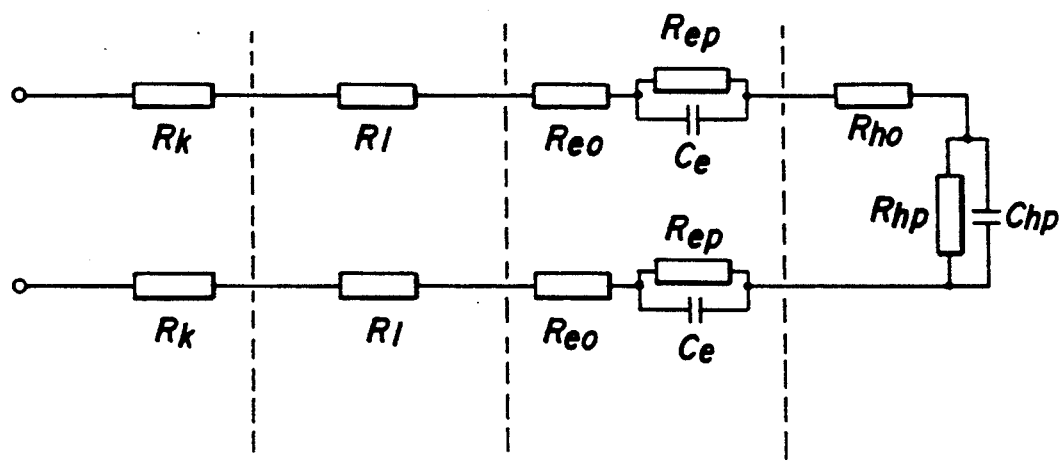
FIG. 1 shows an equivalent network diagram of the actual load characteristics.

FIG. 1 shows an equivalent network diagram of actual load characteristics. FIG. 1 illustrates a contact resistor $R_K$, a line resistor $R_l$, an electrode resistor shown as the resistors, Reo, Rep connected in series and the capacitor Ce connected in parallel with Rep, and the principal resistor Rho, Rhp with the parallel capacitor Chp.

Figure 2:
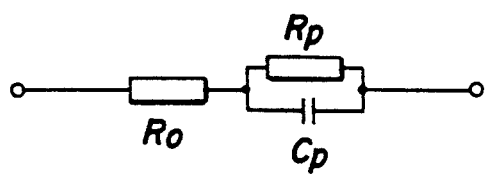
FIG. 2 shows a simplified equivalent network diagram according to FIG. 1.

FIG. 2 illustrates a simplified equivalent network diagram, with series resistors Ro, Rp and the parallel capacitor Cp.

Figure 3:
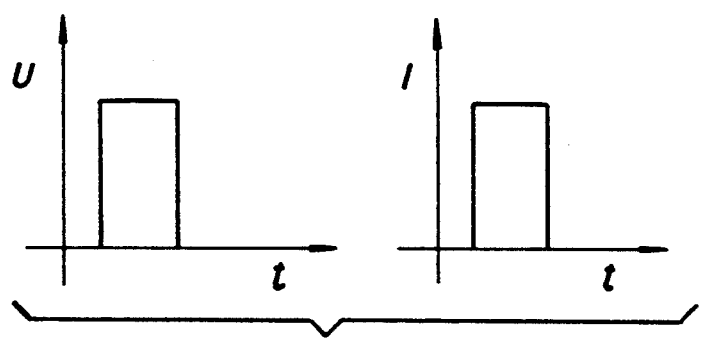
FIG. 3 shows voltage and current pulse forms measured at 1 KOhm.
Figure 4:
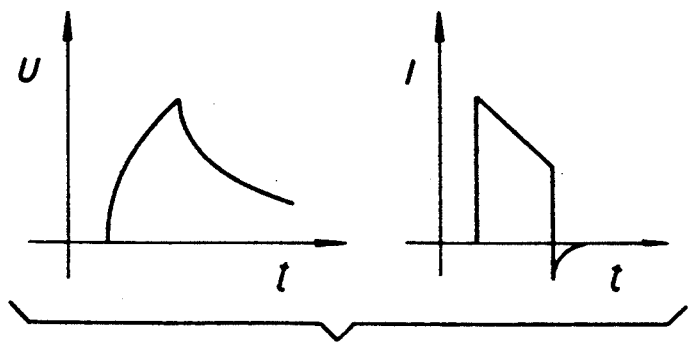
FIG. 4 shows voltage and current pulse forms measured on a test patient.

FIG. 3 shows the voltage and current pulse form measured at 1 KOhm, and FIG. 4 shows the voltage and current pulse form obtained by measurements on the test patient at the same scale. A comparison of FIGS. 3 and 4 illustrates a significant deviation. It is seen that the current is higher by about 10 to 40% at the patient than at the 1 KOhm measuring resistor.

Figure 5:
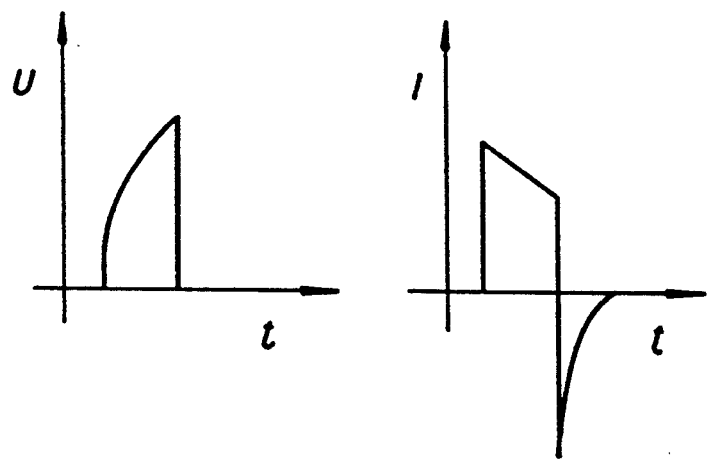
FIG. 5 shows voltage and current pulse forms obtained with the cutoff short circuit.
Figure 6:
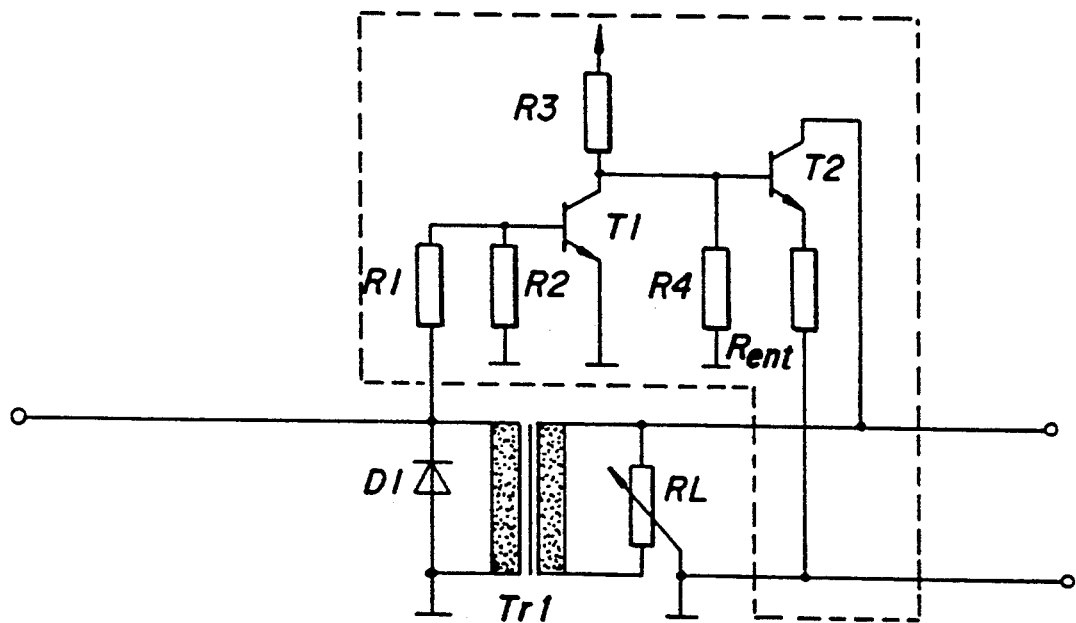
FIG. 6 shows the cutoff short circuit layout.

FIG. 5 displays the voltage and current pulse form obtained by the circuit according to FIG. 6.

The output short circuit network according to FIG. 6 includes a transistor T1, which activates a subsequent transistor T2 upon actuation by a triggering signal. The collector of T1 is connected to the base of T2. The actuating pulse is inverted in the transistor T1, whereby the transistor T2 switches to the negative pulse flank (FIG. 5) and the outlet is short-circuited by the discharge resistor Rent connected to the emitter side. The body contact capacitor, which is charged during the pulse, is discharged very rapidly in this manner. Upon the next positive actuating flank, T2 blocks and the pulse arrives at the patient.

In therapy, pulse repeat frequencies of up to about 160 Hz are used advantageously. At higher frequencies, the body capacitor is charged by the subsequent pulse before it has been completely discharged. This leads to very slight cellular tissue excitation by increasing frequencies.

The circuit according to the invention greatly accelerates the discharge of the body capacitor and may be used advantageously in all TNS devices of a similar design. The therapeutic effect against pain is thereby greatly enhanced.

I claim:

1. An apparatus for transcutaneous electric nerve stimulation (TNS) comprising:
   a frequency generator;
   an electric circuit means for generation of different output frequencies of variable intensity at output electrodes; and
   an output short circuit network to improve an emitted pulse form, said output short circuit network comprising at least a first transistor and a second transistor, upon actuation of said first transistor by a triggering pulse, a collector of said first transistor activates a base of said second transistor, said output short circuit network being configured such that the triggering pulse is inverted in the first transistor, and the second transistor switches the pulse form to a negative pulse flank and an output of the second transistor is short-circuited by a discharge resistor connected to the second transistor emitter.

2. An apparatus according to claim 1, wherein a base of said first transistor is connected by an inlet resistor R1 to an actuation signal.

3. An apparatus according to claim 2, wherein a collector of said second transistor is connected to a first outlet pole and the discharge resistor is connected to the second transistor emitter and a second outlet pole.

4. An apparatus according to claim 3, wherein a maximum pulse form repeat frequency is about 160 Hz.

5. An apparatus according to claim 1, wherein a current pulse form is saw-tooth-like, with a steep negative descent flank.

6. An apparatus according to claim 1, wherein a voltage pulse form exhibits an ascent with a steep beginning and a flattened portion to a maximum, which then declines steeply.

7. An apparatus according to claim 1, wherein an equivalent network diagram of said output short circuit network is a series of horizontal load resistors, together with a capacitor connected in parallel to one of the resistors.

8. A transcutaneous electric nerve stimulation device comprising:
   means for generating a pulse form connected to a power supply and a frequency generator;
   a pulse shaping unit, connected to said means for generating a pulse form including a first transistor inverting stage connected to a triggering signal, and a second negative pulse flank switching transistor stage configured to short an output of said means for generating with a discharge resistor, wherein a collector of said first transistor stage is connected to a base of said second transistor stage.

9. A stimulation device according to claim 8, further comprising an inlet resistor connected between said triggering signal and a base of said first transistor stage.

10. A stimulation device according to claim 9, wherein a collector electrode of said second transistor stage is connected to a first outlet pole of said pulse generation system and said discharge resistor is connected between an emitter of said second transistor stage and a second outlet pole of said pulse generation system.

11. A stimulation device according to claim 8, wherein a maximum pulse form repeat frequency is about 160 Hz.

12. A stimulation device according to claim 8, configured to generate a saw-tooth current pulse form with a steep negative descent flank.

13. A stimulation device according to claim 8, configured to generate a voltage pulse with an ascent portion exhibiting a steep beginning, a flattened portion to a maximum and a steep decline.

14. A method for generating a transcutaneous electric nerve stimulation pulse comprising the steps of:
   generating a triggering pulse;
   generating an output signal based in part on said triggering pulse; and
   modifying said output signal in response to said triggering pulse, wherein said step of modifying comprises at least the steps of inverting said triggering pulse, and shorting said output signal.

15. A method according to claim 14, wherein said step of shorting comprises the step of connecting a resistive load across poles of said output signal.

* * * * *